US009221856B2

(12) United States Patent
Rosenthal et al.

(10) Patent No.: US 9,221,856 B2
(45) Date of Patent: Dec. 29, 2015

(54) METHOD FOR PURIFYING A CRUDE PNPNH COMPOUND

(71) Applicants: SAUDI BASIC INDUSTRIES CORPORATION, Riyadh (SA); LINDE AG, Munich (DE)

(72) Inventors: Uwe Rosenthal, Lambrechtshagen (DE); Bernd H. Müller, Rostock (DE); Normen Peulecke, Rostock (DE); Marco Harff, Munich (DE); Anina Wöhl, Munich (DE); Andreas Meiswinkel, Munich (DE); Heinz Bölt, Wolfratshausen (DE); Wolfgang Müller, Munich (DE); Abdullah Mohammad Al-Qahtani, Riyadh (SA); Mohammed H. Al-Hazmi, Riyadh (SA); Shahid Majeed Azam, Riyadh (SA)

(73) Assignees: SAUDI BASIC INDUSTRIES CORPORATION, Riyadh (SA); LINDE AG (DE)

( * ) Notice: Subject to any disclaimer, the term of this patent is extended or adjusted under 35 U.S.C. 154(b) by 0 days.

(21) Appl. No.: 14/176,571

(22) Filed: Feb. 10, 2014

(65) Prior Publication Data

US 2014/0228580 A1 Aug. 14, 2014

(30) Foreign Application Priority Data

Feb. 11, 2013 (EP) .................................... 13154780

(51) Int. Cl.
  *C07F 9/6587* (2006.01)
  *C07F 9/6584* (2006.01)
  *B01J 31/14* (2006.01)
  *B01J 31/18* (2006.01)
  *C07F 9/48* (2006.01)

(52) U.S. Cl.
  CPC ............. *C07F 9/6587* (2013.01); *B01J 31/143* (2013.01); *B01J 31/189* (2013.01); *C07F 9/4883* (2013.01); *C07F 9/65848* (2013.01); *B01J 2231/20* (2013.01); *B01J 2531/62* (2013.01)

(58) Field of Classification Search
  CPC ... C07F 9/4883; C07F 9/65848; C07F 9/6587
  See application file for complete search history.

(56) References Cited

U.S. PATENT DOCUMENTS

2014/0228594 A1  8/2014  Rosenthal et al.
2014/0228608 A1  8/2014  Al-Qahtani et al.

FOREIGN PATENT DOCUMENTS

EP  2239056 A1  10/2010
EP  2239056 B1  7/2011
WO  0204119 A1  1/2002
WO  2009006979 A2  1/2009

OTHER PUBLICATIONS

Peitz et al. "Metalation and Transmetalation Studies on Ph2PN(iPr)P(Ph)N(iPr)H for Selective Ethene Trimerization to 1-Hexene" Organometallics, 2010, vol. 29, pp. 5263-5268.*
Aluri et al. Coordination chemistry of new selective ethylene trimerisation ligand Ph2PN(iPr)P(Ph)NH(R) (R=iPR, Et) and tests in catalysis Dalton Transations, 2010, vol. 39, pp. 7911-7920.*
European Search Report for EP13154794 mailed Mar. 7, 2013, 1 page.
Written Opinion of the International Searching Authority for PCT/IB2014/058921 mailed Apr. 16, 2014, 6 pages.
Written Opinion of the Intl Searching Authority for PCT/IB2014/058917 mailed Apr. 14, 2014, 10 pages.
Aluri, B., et al., "Coordination chemistry of new selective ethylene trimerisation ligand Ph2PN(iPr)P(Ph)NH(R)(R=iPr, Et) and tests in catalysis", Dalton Transactions, 39, 7911-7920 (2010).
Dulai, Arminderjit, et al., "N,N'-Bis(diphenylphosphino)diaminophenylphosphine Ligands for Chromium-Catalyzed Selective Ethylene Oligomerization Reactions", Organometallics, 30, 935-941 (2011).
European Search Report; EP13154784.6-1352; Date of completion of the search Aug. 30, 2013; 14 pages.
Muller, B, et al, "Synthesis and Reactions of the Homoleptic Chromium (II) Bis-amide [Ph 2 PN(i Pr)P(Ph)N(iPr)-]-]2Cr with Relevance to a Selective Catalytic Ethene Trimerization System to 1-Hexene", Organometallics, 31, 3695-3699 (2012).
International Search Report; International Application No. PCT/IB2014/058917; Feb. 11, 2014; 7 pages.
International Search Report; Internatonal Application No. PCT/IB2014/058919; Feb. 11, 2014; 4 pages.
Written Opinion; International Application No. PCT/IB2014/058919; Nov. 2, 2014; 6 pages.
International Search Report; International Application No. PCT/IB2014/058921; Feb. 11, 2014; 4 pages.
Peitz, Stephan, et al. "Activation and Deactivation by Temperature: Behavior of Ph2PN(iPr)P(Ph)N(iPr)H in the Presence of Alkylaluminum Compounds Relevant to Catalystic Selective Ethene Trimerization", Chemisty—A European Journal, vol. 16, No. 40, 12127-12132 (Oct. 2011).
Peitz, Stephan, "A Selective Chromium Catalyst System for the Trimerization of Ethene and Its Coorination Chemistry", European Journal of Inorganic Chemistry, 1167-1171 (Feb. 2010).
Peitz, Stephan, et al. "Heterobimetallic Al—Cl—Cr Intermediates with Relevance to the Selective Catalytic Ethene Trimerization Systems Consisting of CrCl3(THF)3, the Aminophosphorus Ligands Ph2PN(R)P(Ph(N(R)H, and Triethylaluminum", Organometalics 30, 2364-2370 (2011).
Peitz, S, et al., "Metalation and Trasmetalation Studies on Ph2PN(iPr)P(Ph)N(iPr)H for Selective Ethene Trimerization to 1-Hexene", Organometallics, 29, 5263-5268 (2010).
International Preliminary Report on Patentability and Written Opinion for International Application No. PCT/IB2014/058919, Application Filing Date—Feb. 11, 2014, Date of Mailing Aug. 20, 2015, seven pages.

(Continued)

*Primary Examiner* — Joseph Kosack
(74) *Attorney, Agent, or Firm* — Cantor Colburn LLP

(57) ABSTRACT

The present invention relates to a method for purifying a crude PNPNH compound by metalation and re-protonation.

18 Claims, No Drawings

(56) References Cited

OTHER PUBLICATIONS

International Preliminary Report on Patentability and Written Opinion for International Application No. PCT/IB2014/058917; Application Filing Date Feb. 11, 2014; Date of Mailing Aug. 20, 2015, 11 pages.
International Preliminary Report on Patentability and Written Opinion for International Application No. PCT/IB2014/058921, Application Filing Date Feb. 11, 2014, Date of Mailing Aug. 20, 2015, seven pages.
International Search Report for International Application No. PCT/IB2015/050077; Application Filing Date—Jan. 5, 2015; Date of Mailing—Aug. 11, 2015, six pages.
Written Opinion for International Application No. PCT/IB2015/050077; Application Filing Date—Jan. 5, 2015; Date of Mailing—Aug. 11, 2015, seven pages.

\* cited by examiner

METHOD FOR PURIFYING A CRUDE PNPNH COMPOUND

BACKGROUND

The present invention relates to a method for purifying a crude PNPNH-compound.

Compounds having the general structure PNPNH are well known ligand systems which can be successfully used in a catalyst for the oligomerization of ethylene. Here, they function as ligands to be reacted with, preferably, chromium catalysts. Together with a suitable cocatalyst such a system is effective in the di-, tri- and/or tetramerization of ethylene.

For example, EP 2 239 056 B1 describes a catalyst composition and a process for the di-, tri- and/or tetramerization of ethylene. The catalyst composition comprises a chromium compound, a ligand of the general structure $R_1R_2P$—N($R_3$)—P($R_4$)—N($R_5$)—H and a co-catalyst acting as activator. The ligand's substituents $R_1$, $R_2$, $R_3$, $R_4$, and $R_5$ are independently selected from a number of functional groups, comprising (among others) $C_1$-$C_{10}$-alkyl, aryl and substituted aryl. The chromium source is selected from $CrCl_3(THF)_3$, Cr(III)acetyl acetonate, Cr(III)octanoate, Cr-hexacarbonyl, Cr(III)-2-ethylhexanoate and (benzene)tricarbonyl-chromium (wherein THF is tetrahydrofuran). The co-catalyst or activator is trimethylaluminum, triethylaluminum, triisopropylaluminum, triisobutylaluminum, ethylaluminumsesquichloride, diethylaluminum chloride, ethylaluminum dichloride, methylaluminoxane, or a combination comprising at least one of the foregoing.

A preferred choice of catalyst constituents comprises $CrCl_3(THF)_3$ as chromium source, triethylaluminum as activator, and $(Ph)_2P$—N(i-Pr)—P(Ph)-N(i-Pr)—H as ligand for the catalytically active complex as shown below

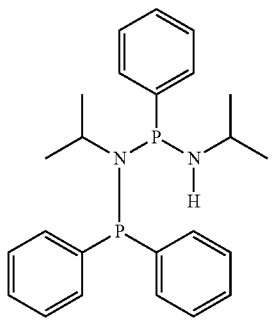

where Ph is a phenyl group and i-Pr is an isopropyl group. This ligand features the typical PNPN—H-backbone, which is why this class of compounds, regardless of the precise nature of its substituents, is often referred to as a "PNPNH-ligand."

WO 2009/006979 A2 describes essentially modified catalyst systems of the general type already disclosed in EP 2 239 056 B1. These modified systems take advantage from the same PNPNH-type ligands. However, now a "modifier" is added to the system, for example ammonium or phosphonium salts of the type $[H_4E]X$, $[H_3ER]X$, $[H_2ER_2]X$, $[HER_3]X$ or $[ER_4]X$ (with E=N or P, X=Cl, Br or I and R=alkyl, cycloalkyl, acyl, aryl, alkenyl, alkynyl etc.).

Preferred embodiments of the invention disclosed in WO 2009/006979 A2 involve, for instance, modifiers such as tetraphenylphosphonium chloride, tetraethylammonium chloride-monohydrate, triethylamine-hydrochloride etc. Also, as a "type $[ER_4]X$"-modifier, dodecyltrimethylammonium chloride can advantageously be used, due to its low price, abundant supply and good solubility in the reaction solution.

In fact, the specifically designed coordination behaviour of the PNPNH ligands is largely the origin of the high selectivities of the catalytically active chromium complexes. Clearly, the high product selectivities are of great importance for the economic viability of the technical process.

Of course, a high selectivity directly results in a minimization of undesired side products in the technical oligomerization process. It is therefore evident that the "key ingredients" of the catalyst have to be produced on technical scale with the highest possible quality.

The laboratory procedure for the preparation of the PNPNH ligand, as demonstrated in example 1 below, gives a material of a good quality.

Using the ligand from the laboratory bench-scale synthesis in standardised catalytic tests of the ethylene trimerization to 1-hexene, it is easily possible to obtain overall 1-hexene yields of 91-93 weight percent at 1-hexene purities of 99.0-99.3% with hardly any detectable wax/polymer formation.

While being transferred to technical scale, however, this laboratory procedure regularly needs some modifications so as to meet the requirements imposed by boundary conditions in a technical environment. For example, in order to avoid hot spots in the reaction mass, it might be advisable to change the dosing sequence and/or dosing speed of some of the ingredients. Furthermore, reaction temperatures as low as −40° C. will, most likely, turn out to be unfavourable or even not feasible on technical scale. Moreover, solvents may have to be recycled, resulting in the need to vary the nature of the solvent or to use solvent mixtures. Even after optimization of the ligand's production process on technical scale, it does not seem to be possible to reach a ligand quality, i.e., purity, comparable to the product synthesized using the laboratory procedure.

One of the most severe problems in all known technical-scale oligomerization processes is the formation of long-chain by-products such as waxes and polyethylene. Clearly, this leads to frequent fouling of equipment such as reactor inner surfaces, heat exchangers, etc. Moreover, wax or polymer formation can lead to plugging of tubing, valves, pumps, and other equipment, making frequent plant shut downs for purging/cleaning and maintenance of equipment necessary.

The measured formation rate of waxes/polymers has to be considered in the design of a commercial ethylene oligomerization plant. Adequate minimization measures and handling procedures for these undesired by-products are inevitable in order to allow for commercially successful plant operation.

Having in mind that, as already pointed out above, a high selectivity results directly in a minimization of undesired side products in this technical process, the "key ingredients," i.e. especially the ligand, has to be produced on technical scale with the highest possible quality.

The attempt to purify crude PNPNH compound by vacuum distillation using a thin-film evaporator turned out to be rather unsuccessful, since there was hardly any separation effect between the ligand and the impurities.

There accordingly remains a need in the art for a method for purifying a crude PNPNH compound (ligand).

SUMMARY

A method for purifying a crude PNPNH compound of the general structure

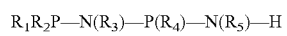

wherein $R_1$, $R_2$, $R_3$, $R_4$ and $R_5$ are independently selected from halogen, amino, trimethylsilyl, $C_1$-$C_{10}$-alkyl, substituted $C_1$-$C_{10}$-alkyl, $C_6$-$C_{20}$-aryl and substituted $C_6$-$C_{20}$-aryl, or any cyclic derivative wherein at least one of the P or N atoms of the PNPN—H structure is a member of a ring system, the ring system being formed from one or more constituent compounds of the PNPNH-structure by substitution, comprising the steps:

a) dissolving the PNPNH-compound in a first solvent;
b) metalating the PNPNH-compound;
c) isolating the metalated compound obtained in step b), preferably by precipitating the metalated compound obtained in step b), separating the metalated compound and the solvent and optionally washing the separated metalated compound with the solvent;
d) re-protonating the metalated compound in a second solvent, and
e) optionally removing the solvent and optionally recrystallizing the re-protonated PNPNH ligand.

DETAILED DESCRIPTION

As used herein, the term PNPNH is to be understood to represent the general structure $R_1R_2P$—$N(R_3)$—$P(R_4)$—$N(R_5)$—H.

The present invention is related to the purification of a crude PNPNH compound. As the term "crude" might be somewhat open and unclear, the method of the present invention is to be understood that the PNPNH compound obtained after being processed in the inventive method has higher purity than the starting material. That means, the extent of purity of the "crude" starting material is not relevant, as long as the final product obtained has a higher purity than the starting material.

As is to be understood, any cyclic derivative of the PNPNH compound can be utilized, wherein at least one of the P or N atoms of the PNPN-unit is a ring member, or any cyclic derivative wherein at least one of the P or N atoms of the PNPN—H structure is a member of a ring system, the ring system being formed from one or more constituent compounds of the PNPNH-structure by substitution, i.e., .e., by formally eliminating per constituent compound either two whole groups $R_1$-$R_5$ (as defined above) or H, one atom from each of two groups $R_1$-$R_5$ (as defined above) or a whole group $R_1$-$R_5$ (as defined above) or H and an atom from another group $R_1$-$R_5$ (as defined above), and joining the formally so created valence-unsaturated sites by one covalent bond per constituent compound to provide the same valence as initially present at a given site. In an embodiment, the ring is formed by substitution of one or more, preferably two of the constituents of one PNPNH molecule. In other words, the cyclic derivative can include a ring system formed by removal of two of groups $R_1$-$R_5$ (as defined above) or H from one PNPNH molecule, with formation of a covalent bond in place of the groups. The cyclic derivative can include a ring system formed by removal of an atom from two of the groups $R_1$-$R_5$ (as defined above) or H from one PNPNH molecule, with formation of covalent bond in place of the atoms. Alternatively, the cyclic derivative can be formed by removal of one of the groups $R_1$-$R_5$ (as defined above) or H from one PNPNH molecule, and an atom from one of the groups $R_1$-$R_5$ (as defined above) or H from the same PNPNH molecule, with formation of a covalent bond in place of the removed group and the atom.

Suitable cyclic derivatives can be as follows:

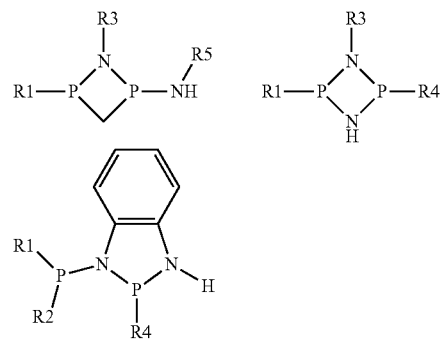

A preferred solvent for dissolving the crude PNPNH compound in step a) can be selected from toluene, n-hexane, cyclohexane, 1-hexene or a combination comprising at least one of the foregoing, preferably toluene.

The separation in step c) can be preferably achieved by filtration or centrifugation. The optional washing can be done with pure solvent.

In optional step e) recrystallization is achieved by use of a suitable aromatic or aliphatic solvent, preferably by the mixture of an aromatic and aliphatic solvent. Most preferably is toluene or n-hexane or a mixture thereof.

The inventive method yields a white crystalline powder with a melting point of 58° C. and a purity in excess of 99.9 weight percent. The purified ligand can be directly used in a selective ethylene-oligomerization process.

In an alternative, a solution containing the re-protonated compound obtained in step d) can also be directly used for the catalytic oligomerization, thus skipping the removal of solvent with subsequently recrystallization in step e). This is especially always possible whenever the corresponding base of the acid added in step d) does not interfere with the oligomerization reaction. This is, for example, the case when ammonium chloride is used for re-protonation.

Preferably, the first and second solvents are identical.

It is in general preferred, that the first and/or second solvent is (are) non-polar solvents, preferably selected from aromatic and/or aliphatic solvents, preferably toluene, n-hexane, cyclohexane, and 1-hexene.

Further, metalating in step b) is preferably achieved by adding an organometallic compound, a base, sodium or potassium metal in an amount equivalent to or in excess of the molar concentration of the PNPNH ligand into the solution obtained in step a).

Also, metalation is preferably achieved by adding n-butyl lithium, sec-butyl lithium, tert-butyl lithium, sodium cyclopentadienide, sodium hydride, sodium amide, alkyl- or aryl magnesium halides (Grignard reagents), sodium bis(trimethylsilyl) amide, dialkylmagnesium, diarylmagnesium, trialkylaluminium, dialkylzinc, sodium or potassium metal, preferably n-butyllithium.

In addition, re-protonation in step d) is preferably achieved by addition of an acid, preferably a weak acid.

Finally, the acid is preferably an ammonium halogenide, preferably ammonium chloride, phosphoric acid, hydrogen sulphite, and boric acid. It was surprisingly found that it is the quality/purity of the ligand system in a process for oligomerization of ethylene which is essential for avoiding wax/polyethylene formation. PE/wax formations of less than 0.10 weight percent, based on the total amount of oligomers/polymers obtained in such a process, can be achieved, while ligand systems prepared according to the art resulted in PE/wax formation of significantly higher amounts.

Utilizing the purified PNPNH ligand obtained by the present method in the oligomerization of ethylene provides strong reduction of side-product wax and polyethylene formation, extension of oligomerization equipment's time on stream, less frequent shutdowns for purging, cleaning and maintenance, mitigation of equipment fouling, lower chances of operational upset conditions due to plugged equipment and, in summary, improvement of the plant operability in general.

As a further surprising fact, it was found that none of other possible candidates for the "key factors," i.e. key factors influencing a wax/polyethylene formation, showed any significant or discernable effect on polymer formation. Such further key factors can be, e.g., intrinsic mechanistic reasons linked to the metallocycle mechanism that is considered the origin of the high selectivity towards preferred oligomers, metallic impurities introduced as trace amounts of Fe, Ni, Ti, Zr, etc., along with the catalyst components, surface-induced heterogeneous reactions on the reactor's inner surface, chromium hydride species, radical polymerisation mechanisms or unfavourable oxidation states of chromium.

As starting point for an effective purification method for the PNPNH compound, considerable effort was put into the investigation of the chemical nature of the impurities. The structure of some of these impurities, as identified in the crude material after synthesis by $^{31}$P-NMR and/or mass spectroscopy, are shown in Example 1 below.

These impurities were detected and characterized during a scale-up of the laboratory method to technical scale (approximately 20-100 kg per batch) using $^{31}$P-NMR and/or mass spectrometry. The amount of each impurity in the crude ligand material varies, according to the crude ligand sample's history. Some of the impurities originate from the synthesis itself, others are reaction products with trace amounts of oxygen or water. The fact that the ligand is susceptible to water and air/oxygen is also important for the purification procedure as any contact with water and oxygen has to be preferably avoided.

As already pointed out above, it was surprisingly found that by metalation of a PNPNH compound, the metalated compound can be easily separated from the impurities, as the metalated species regularly shows a poor solubility in the solvents to be typically used in the production process of the PNPNH compound and/or the oligomerization reaction. Preferred metalated species PNPN-M are those with M=Li, Mg, Na, K, Cr, Al and Zn. While specific examples of metalation reagents are given above, a PNPN—Cr compound can be preferentially obtained via transmetalation of the respective Mg-compound using CrCl$_2$(THF)$_2$ (under release of MgCl$_2$ and 2 THF). The Mg-metalated compound, in turn, can be obtained by reacting the PNPNH ligand with any metalating magnesium compound, such as Mg-alkyls or alkyl magnesium halides, such as butylethyl magnesium or isobutyl magnesium chloride.

Additional advantages and features of the present invention are now illustrated in the following example section.

EXAMPLES

Example 1

Ligand Preparation, Laboratory Scale

Preparation of Bis(isopropyl-amino-)phenylphosphine (NPN)

To a stirred solution of isopropylamine (30 ml, 352 mmol) in diethyl ether (250 ml), dichlorophenylphosphine (9.63 ml, 71 mmol, dissolved in 50 ml diethylether) was added at 0° C. over a period of 30 min. After stirring for a total of 72 hrs the solution was filtered. The residue was washed with diethylether and the solvent was removed in vacuum. The remaining oil was distilled at 0.2 Torr/76-78° C. to give a colorless liquid with 33% yield (5.3 g). $^{31}$P {H} NMR: 49.0 ppm.

Some impurities found in the crude Ph$_2$P—N(i-Pr)—P(Ph)-N(i-Pr)—H-ligand after synthesis are shown below.

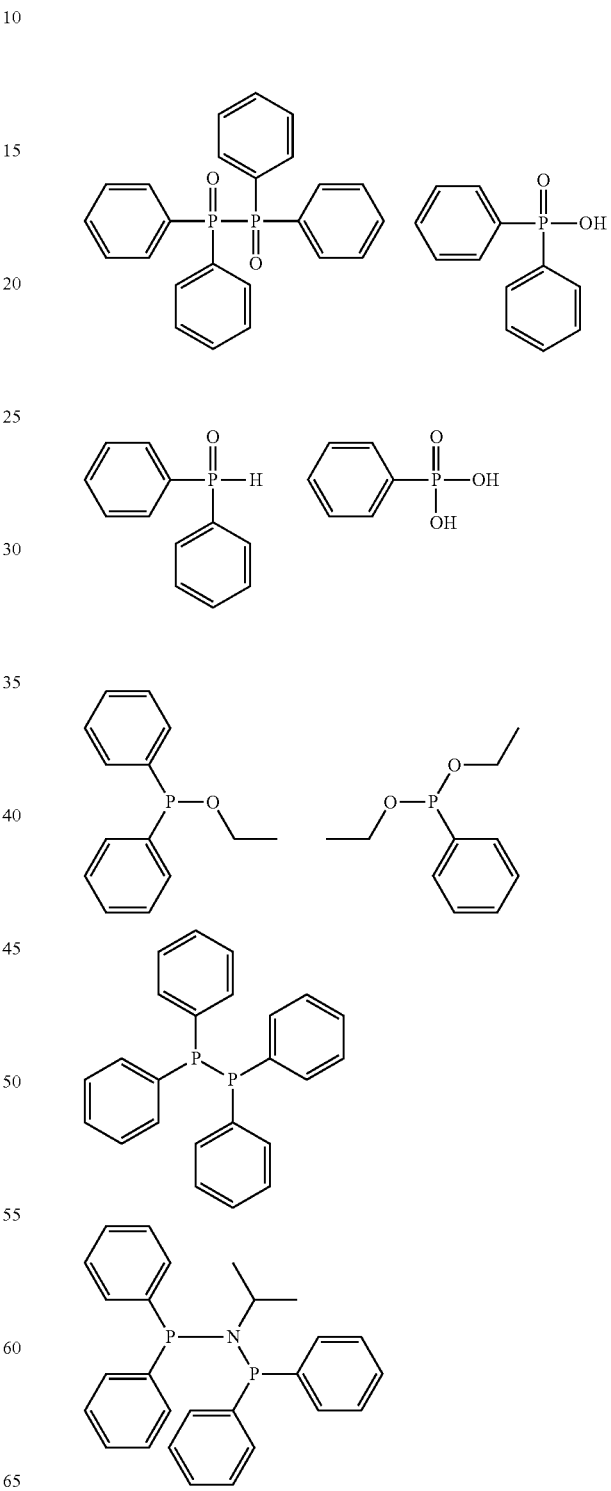

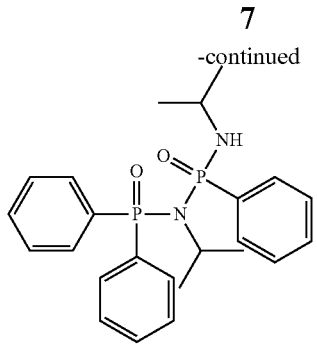

Preparation of (Ph)₂PN(i-Pr)P(Ph)NH(i-Pr) (PNPN—H)

A solution of the NPN-species (2.4 g, 10.7 mmol) in tetrahydrofuran (10 ml) was added dropwise to a stirred solution of triethylamine (6 ml) and chlorodiphenylphosphine (2.36 g, 10.7 mmol) in THF (40 ml) at −40° C. After additional stirring for 24 hrs at room temperature the triethylammonium salt was filtered off and the residue was dissolved in n-hexane, filtrated again, and the solution was kept at −30° C. for crystallisation. Yield 52% (2.3 g, 5.6 mmol). $^{31}$P {H} NMR: 41.2, 68.4 (broad).

Example 2

Preparation of [Ph₂PN(i-Pr)P(Ph)N(i-Pr)—Li]₂

Ph₂PN(i-Pr)P(Ph)N(i-Pr)—H (8.70 g, 21.35 mmol) was dissolved in 15 ml of toluene. After cooling down to −78° C., n-butyllithium (12.8 ml, 2.5 M n-BuLi in n-heptane, 32.0 mmol) was added to the solution, causing the color to change immediately to orange/yellow. The solution was stirred for additional two hours at room temperature and a colorless solid precipitated. The precipitate was filtered and washed three times with 5 ml toluene. Remaining solvent was removed in vacuum to give a colorless powder. Yield: 6.73 g (76%). Molecular weight: 414.39 g/mol [C₂₄H₂₉LiN₂P₂]. Elementary analysis: calc.: C, 69.56%; H, 7.05; &, N, 6.76%. found: C, 69.25%; H, 7.06%; N, 6.87%. Melting point: 187-189° C. $^1$H NMR (THF-d₈) δ=−7.50-7.57 (m, 6H, aryl-H), 7.20-7.34 (m, 6H, aryl-H), 7.02 (m, 2H, arom.), 6.93 (m, 1H, aryl-H), 3.70 (m, 1H, CHCH₃), 3.58 (m, 1H, CHCH₃), 1.39 (d, J=6.47 Hz, 3H, CHCH₃), 1.25 (d, J=6.23 Hz, 3H, CHCH₃), 1.22 (d, J=6.24 Hz, 3H, CHCH₃), 1.04 (d, J=6.55 Hz, 3H, CHCH₃); $_{13}$C-NMR (THF-d₈): δ=143.4, 142.0, 134.9, 133.4, 132.5, 131.5, 129.4, 128.6, 128.0, 127.9, 127.1, 125.2 (arom.), 54.6, 54.0 (CHCH₃), 31.0, 26.7 (CHCH₃); $^{31}$P {H} NMR (THF-d₈): δ=40.6 (br), 100.1 pp, (d, $^2J_{P-P}$=24.6 Hz).

Example 3

Ligand Purification via Metalation of the PNPN—H Ligand with subsequent Re-Protonation The crude ligand (8.70 g, 21.35 mmol) was dissolved in 15 ml of toluene. Under cooling n-butyllithium (12.8 ml, 2.5 M n-BuLi in n-heptane, 32.0 mmol) was added to the solution, causing the color to change immediately to orange/yellow. The solution was stirred for additional two hours at room temperature and colorless solid precipitated. The precipitate was filtered and washed with 5 ml toluene. The residue and ammonium chloride (1.70 g, 32 mmol) were suspended in toluene. This suspension was stirred for 10 h. Filtration results in a toluene solution of purified ligand, which can be used without further treatment in catalytic reactions. Alternatively, the solvent was removed in vacuum to yield 5.41 g (62%). Molecular weight: 408.19 g/mol [C₂₄H₃₀N₂P₂]. Elementary analysis: calc. C, 70.57%; H, 7.40%; N, 6.86%. found; C, 70.50%; H, 7.35%; N, 6.87%.

Also, the lithiated compound gives sufficient analytical results: [Ph₂PN(i-Pr)P(Ph)N(i-Pr)Li]₂, Molecular weight: 414.39 g/mol [C₂₄H₂₉LiN₂P₂]. Elementary analysis: calc. C, 69.56%; H, 7.05%; N, 6.76%. found: C, 69.25%; H, 7.06%; N, 6.87%.

The metalation of a specific PNPNH compound is shown in the equation below, wherein M is a metal, $^i$Pr is isopropyl and Ph is phenyl.

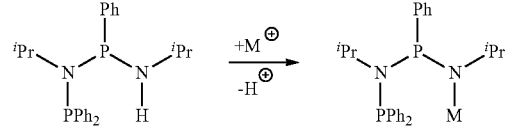

Example 4

A standard ethylene oligomerization (trimerization to 1-hexene) was carried out and ligands prepared by different purification techniques were utilized. The PE/wax formation was measured. The results are given in Table 1.

Table 1 shown the correlation between (Ph)₂P—N(i-Pr)—P(Ph)-N(i-Pr)—H-ligand purity and polyethylene/wax formation during ethylene trimerization to 1-hexene, measured in a standard performance test. Standard reaction conditions are: $p_{ethylene}$=30 bar, T=50° C., co-catalyst= triethylaluminum, modifier=dodecyltrimethylammonium chloride, residence time=60 min, [Cr]=0.3 mmol/l, [Ligand[/[Cr]=1.75, [Al]/[Cr]=25, [Cl]/[Cr]=8 (all ratios in molar units).

TABLE 1

| | Ligand purification technique | Appearance | Purity ($^{31}$P-NMR, GC), wt %* | PE/wax formation during catalytic ethylene trimerization (standard reaction conditions), wt %* |
|---|---|---|---|---|
| 1 | Crude PNPN-H directly from synthesis on technical scale | Yellow, high-viscosity liquid ("honey-like") | 75-80 | 1.0-1.5 |
| 2 | Distilled PNPN-H (low pressure thin-film evaporator) | Yellow, high-viscosity liquid ("honey-like") | 86-87 | 0.8-1.0 |
| 3 | Recrystallization of PNPN-H from hexane-solution | White crystalline powder | 98.6 | <0.55 |

TABLE 1-continued

| | Ligand purification technique | Appearance | Purity ($^{31}$P-NMR, GC), wt %* | PE/wax formation during catalytic ethylene trimerization (standard reaction conditions), wt %* |
|---|---|---|---|---|
| 4 | Purification of PNPN-H using metalation with butyllithium and subsequent re-protonation | White crystalline powder, m.p. 58° C. | 99.9 | <0.10 |

*wt %, based on total amounts of oligomers/polymers obtained

In summary, method for purifying a crude PNPNH compound of the general structure $$R_1R_2P\text{—}N(R_3)\text{—}P(R_4)\text{—}N(R_5)\text{—}H$$

wherein $R_1$, $R_2$, $R_3$, $R_4$ and $R_5$ are independently halogen, amino, trimethylsilyl, $C_1$-$C_{10}$-alkyl, substituted $C_1$-$C_{10}$-alkyl, $C_6$-$C_{20}$-aryl and substituted $C_6$-$C_{20}$-aryl, or any cyclic derivative wherein at least one of the P or N atoms of the PNPN—H structure is a member of a ring system, the ring system being formed from one or more constituent compounds of the PNPNH-structure by substitution, preferably the ring system being formed from two constituents of the same PNPNH-structure by substitution, more preferably wherein the PNPNH compound is (Ph)$_2$P—N(i-Pr)—P(Ph)-N(i-Pr)—H, (Ph)$_2$P—N(i-Pr)—P(Ph)-N(Ph)-H, (Ph)$_2$P—N(i-Pr)—P(Ph)—N(tert-butyl)-H, (Ph)$_2$P—N(i-Pr)—P(Ph)—N(CH(CH$_3$)(Ph))—H, comprising: (a) dissolving the PNPNH-compound in a first solvent; (b) metalating the PNPNH-compound, preferably wherein metalating in step b) i by adding an organometallic compound, a base, sodium metal, or potassium metal, preferably n-butyl lithium, sec-butyl lithium, tert-butyl lithium, sodium cyclopentadienide, sodium hydride, sodium amide, an alkyl- or aryl magnesium halide, sodium bis(trimethylsilyl) amide, dialkylmagnesium, diarylmagnesium, trialkylaluminium, dialkylzinc, sodium metal, or potassium metal, most preferably n-butyl lithium, in an amount equivalent to or in excess of the molar concentration of the PNPNH ligand into the solution obtained in step a)isolating the metalated compound obtained in step b), preferably by precipitating the metalated compound obtained in step b), separating from the solvent and optionally washing with the solvent; (c) re-protonating the metalated compound in a second solvent, preferably wherein re-protonation in step c) is achieved by addition of an acid, preferably a weak acid, most preferably an ammonium halogenide, preferably ammonium chloride, phosphoric acid, hydrogen sulphide or boric acid, and (d) optionally removing the solvent and optionally recrystallizing the re-protonated PNPNH ligand, preferably wherein the first and second solvents are identical, and are a non-polar solvent, preferably an aromatic and/or aliphatic solvent, preferably toluene, n-hexane, cyclohexane, 1-hexene, or a combination comprising at least one of the foregoing.

The singular forms "a," "an," and "the" include plural referents unless the context clearly dictates otherwise. "Or" means "and/or." Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

The features disclosed in the foregoing description, in the claims and in the drawings may, both separately and in any combination thereof, be material for realizing the invention in diverse forms thereof.

What is claimed is:

1. A method for purifying a crude PNPNH compound of the general structure $$R_1R_2P\text{—}N(R_3)\text{—}P(R_4)\text{—}N(R_5)\text{—}H$$

wherein $R_1$, $R_2$, $R_3$, $R_4$ and $R_5$ are independently halogen, amino, trimethylsilyl, $C_1$-$C_{10}$-alkyl, substituted $C_1$-$C_{10}$-alkyl, $C_6$-$C_{20}$-aryl and substituted $C_6$-$C_{20}$-aryl, or any cyclic derivative wherein at least one of the P or N atoms of the PNPN—H structure is a member of a ring system, the ring system being formed from one or more constituent compounds of the PNPNH-structure by substitution, comprising:
a) dissolving the PNPNH-compound in a first solvent;
b) metalating the PNPNH-compound,
c) isolating the metalated compound obtained in step b),
d) re-protonating the metalated compound in a second solvent, and
e) optionally removing the second solvent and optionally recrystallizing the re-protonated PNPNH ligand.

2. The method according to claim 1, wherein the first and second solvents are identical.

3. The method according to claim 1, wherein the first and/or second solvent is a non-polar solvent, or a combination comprising at least one of the foregoing.

4. The method according to claim 1, wherein metalating in step b) is by adding an organometallic compound, a base, sodium metal, or potassium metal in an amount equivalent to or in excess of the molar concentration of the PNPNH ligand into the solution obtained in step a).

5. The method according to claim 4, wherein metalation is by adding n-butyl lithium, sec-butyl lithium, tert-butyl lithium, sodium cyclopentadienide, sodium hydride, sodium amide, an alkyl- or aryl magnesium halide, sodium bis(trimethylsilyl) amide, dialkylmagnesium, diarylmagnesium, trialkylaluminium, dialkylzinc, sodium metal, or potassium metal.

6. The method according to claim 1, wherein re-protonation in step d) is achieved by addition of an acid.

7. The method according to claim 6, wherein the acid is an ammonium halogenide, phosphoric acid, hydrogen sulphide or boric acid.

8. The method according to claim 7, wherein the acid is ammonium chloride.

9. A method for purifying a crude PNPN—H compound comprising a PNPN—H ligand of the general structure $$R_1R_2P\text{—}N(R_3)\text{—}P(R_4)\text{—}N(R_5)\text{—}H$$

wherein $R_1$, $R_2$, $R_3$, $R_4$ and $R_5$ are independently halogen, amino, trimethylsilyl, $C_1$-$C_{10}$-alkyl, substituted $C_1$-$C_{10}$-alkyl, $C_6$-$C_{20}$-aryl and substituted $C_6$-$C_{20}$-aryl, or any cyclic derivative wherein at least one of the P or N atoms of the PNPN—H structure is a member of a ring system, the ring system being formed from one or more constituent compounds of the PNPN—H-structure by substitution, and an impurity, the method comprising:
(i) dissolving the crude PNPN—H compound in a first solvent;
(ii) metalating the PNPN—H ligand,
(iii) separating the metalated PNPN—H ligand from the first solvent and the impurity,
(iv) re-protonating the metalated PNPN—H ligand in a second solvent, and
(v) optionally removing the second solvent and optionally recrystallizing the re-protonated PNPNH ligand, to provide a purified PNPN—H compound.

10. The method according to claim 9, wherein the impurity comprises PNPN—H ligand synthesis products, PNPN—H ligand reaction products with oxygen and/or water, or a combination thereof.

11. The method according to claim 10, wherein the purified PNPN—H compound has a PNPN—H ligand purity greater than 99.9 wt-%.

12. The method according to claim 11, wherein the first solvent and second solvent are the same.

13. The method according to claim 12, wherein the first and second solvent is a non-polar solvent.

14. The method according to claim 13, wherein metalating in step (ii) is by adding an organometallic compound, a base, sodium metal, or potassium metal in an amount equivalent to or in excess of the molar concentration of the PNPN—H ligand into the solution obtained in step (i).

15. The method according to claim 14, wherein metalation is by adding n-butyl lithium, sec-butyl lithium, tert-butyl lithium, sodium cyclopentadienide, sodium hydride, sodium amide, an alkyl- or aryl magnesium halide, sodium bis(trimethylsilyl) amide, dialkylmagnesium, diarylmagnesium, trialkylaluminium, dialkylzinc, sodium metal, or potassium metal.

16. The method according to claim 15, wherein re-protonation in step (iv) is achieved by addition of an acid.

17. The method according to claim 16, wherein the acid is an ammonium halogenide, phosphoric acid, hydrogen sulphide or boric acid.

18. The method according to claim 17, wherein metalation is by adding n-butyl lithium and the acid is ammonium chloride.

* * * * *